United States Patent
Robert et al.

(10) Patent No.: US 9,142,018 B2
(45) Date of Patent: Sep. 22, 2015

(54) METHOD FOR THREE-DIMENSIONAL LOCALIZATION OF AN OBJECT FROM A TWO-DIMENSIONAL MEDICAL IMAGE

(71) Applicants: Normand Robert, Toronto (CA); Eugene Crystal, Toronto, CA (US)

(72) Inventors: Normand Robert, Toronto (CA); Eugene Crystal, Toronto, CA (US)

(73) Assignee: SUNNYBROOK HEALTH SCIENCES CENTRE, Ontario (CA)

( * ) Notice: Subject to any disclaimer, the term of this patent is extended or adjusted under 35 U.S.C. 154(b) by 0 days.

(21) Appl. No.: 14/371,562

(22) PCT Filed: Jan. 16, 2013

(86) PCT No.: PCT/CA2013/050023
§ 371 (c)(1),
(2) Date: Jul. 10, 2014

(87) PCT Pub. No.: WO2013/106926
PCT Pub. Date: Jul. 25, 2013

(65) Prior Publication Data
US 2014/0321710 A1    Oct. 30, 2014

Related U.S. Application Data

(60) Provisional application No. 61/587,469, filed on Jan. 17, 2012.

(51) Int. Cl.
| | |
|---|---|
| *G06K 9/00* | (2006.01) |
| *G06T 7/00* | (2006.01) |
| *A61B 6/12* | (2006.01) |
| *A61B 19/00* | (2006.01) |
| *A61B 6/00* | (2006.01) |

(52) U.S. Cl.
CPC ............ *G06T 7/0016* (2013.01); *A61B 6/12* (2013.01); *A61B 19/5244* (2013.01); *G06T 7/0044* (2013.01); *A61B 6/5294* (2013.01); *A61B 2019/5238* (2013.01); *A61B 2019/5265* (2013.01); *A61B 2019/5466* (2013.01); *G06T 2207/10081* (2013.01); *G06T 2207/10121* (2013.01); *G06T 2207/20016* (2013.01); *G06T 2207/20056* (2013.01); *G06T 2207/30021* (2013.01); *G06T 2207/30204* (2013.01)

(58) Field of Classification Search
None
See application file for complete search history.

(56) References Cited

U.S. PATENT DOCUMENTS

| | | | |
|---|---|---|---|
| 6,196,715 B1 | 3/2001 | Nambu et al. | |
| 6,368,285 B1 | 4/2002 | Osadchy et al. | |
| 6,484,049 B1 | 11/2002 | Seeley et al. | |
| 8,217,961 B2 * | 7/2012 | Chang | ............................ 345/619 |
| 2008/0275666 A1 | 11/2008 | Ohta et al. | |

OTHER PUBLICATIONS

International Search Report under date of mailing of Apr. 12, 2013 in connection with PCT/CA/050023.

* cited by examiner

*Primary Examiner* — Atiba O Fitzpatrick
(74) *Attorney, Agent, or Firm* — Quarles & Brady, LLP

(57) ABSTRACT

A method for determining the three-dimensional location of an object in real-time from a two-dimensional medical image obtained with a medical imaging system is provided. For example, the three-dimensional location of an interventional medical device or a marker positioned on such a device may be determined from a two-dimensional x-ray image obtained with an interventional x-ray imaging system. Template images corresponding to the object under different imaging geometries and orientations are produced and are compared to images acquired with the medical imaging system. Similarity measures, such as normalized cross correlation and normalized similarity integral, are used to determine the similarity between a selected template image and the medical images in different stages of refining the position information for the object.

20 Claims, 6 Drawing Sheets

METHOD FOR THREE-DIMENSIONAL LOCALIZATION OF AN OBJECT FROM A TWO-DIMENSIONAL MEDICAL IMAGE

CROSS-REFERENCE TO RELATED APPLICATIONS

This application represents the national stage entry of PCT International Application No. PCT/CA2013/050023 filed on Jan. 16, 2013, which claims the benefit of U.S. Provisional Patent Application No. 61/587,469 filed on Jan. 17, 2012, the disclosures of which are hereby incorporated by reference in their entirety for all purposes.

BACKGROUND OF THE INVENTION

The field of the invention is systems and methods for medical imaging. More particularly, the invention relates to systems and methods for tracking the location of an interventional medical device, such as a catheter, using a medical imaging system, such as an x-ray imaging system.

The development of new percutaneous devices and treatment techniques has resulted in a significant increase in the use of x-ray guidance to perform minimally invasive therapies. Currently, x-ray fluoroscopy is the standard imaging modality used for guidance in interventional cardiology procedures. The two-dimensional x-ray projection images produced during fluoroscopy provide excellent visualization of interventional medical devices, but inherently lack depth information. In some procedures, such as electrophysiology procedures, it is important to return to the same anatomical location during the procedure. This task cannot be achieved solely by viewing the catheter in a two-dimensional x-ray image because precise manipulation requires three-dimensional localization.

Localization of interventional medical devices in three-dimensional space can be made possible by using bi-plane imaging system, in which a second x-ray view is acquired from a different perspective using a relative geometrical relationship between the first and second view. In anatomical sites subject to rapid motion, simultaneous acquisition from two perspectives is preferable but can only be achieved using a bi-plane catheterization system. These bi-plane catheterization systems are not common and result in increased x-ray radiation being delivered to the patient. Moreover, even for bi-plane systems, there is currently no x-ray based three-dimensional localization technology commercially available; rather, the operator usually relies on a visual estimate supported by a previously obtained roadmap image.

Three dimensional localization technologies using specially designed non-x-ray based catheter tracking systems have been developed and are commonly used clinically. One such system, called CARTO (Biosense Webster, Inc.; Diamond Bar, Calif.), relies upon a small magnetic field sensor located at the distal tip of the catheter. This magnetic field sensor is used to measure an induced magnetic field from external emitters located beneath a patient. Another system, called EnSite™ (St. Jude Medical, Inc.; St. Paul, Minn.), uses an impedance-based localization technique that employs either six external patches placed on a patient, or a multi-polar catheter positioned inside the heart, to track the interventional device. These systems provide accurate localization, but result in significant capital and per-use cost.

One method for three-dimensional localization of an interventional medical device from a two-dimensional x-ray projection image is disclosed in U.S. Pat. No. 6,574,493. In this method, a marker having a specific geometric arrangement is affixed to the interventional device to be tracked. When imaged in two-dimensions, the affixed marker provides an indication of its position and orientation on account of its known, and particular geometric arrangement. Because this method requires use of a specialized marker that is affixed to an interventional medical device, it is of limited clinical use. Namely, the method requires modification of existing interventional devices, and such modifications may negatively affect the performance and safety characteristics of the medical device being used.

Therefore, there exists a need to develop an inexpensive and robust method for tracking the position of an interventional medical device in three-dimensional space using the information available from a single, two-dimensional image acquired with a standard x-ray fluoroscopy system. Fluoroscopy suites are used as a standard imaging modality in virtually all hospitals and, therefore, additional cost to use such a three-dimensional localization technique would be quite low.

SUMMARY OF THE INVENTION

The present invention overcomes the aforementioned drawbacks by providing a method for determining the three-dimensional location of an object, such as an interventional medical device or a marker placed thereon, from a two-dimensional image acquired with a standard medical imaging system, such as an x-ray imaging system or a magnetic resonance imaging system. The location of the object is determined, for example, by iteratively comparing images acquired with the medical imaging system with template images that depict the object as a two-dimensional synthesized projection image of the object at different positions and orientations.

It is an aspect of the invention to provide a method for determining a three-dimensional location of an object using a two-dimensional image obtained with a medical imaging system. The method includes acquiring image data with the medical imaging system and producing an initial image from an image with a reduced information content, such as a down-sampled image data produced by down-sampling the acquired image data by a down-sampling factor. The information content of an image may also be reduced by sub-sampling an initial image and filtering the result if needed to prevent aliasing. An initial position estimate of the three-dimensional location of the object is selected, as is an initial template image of the object using the initial position estimate. The initial template image depicts a synthesized projection image of the object positioned in the medical imaging system at the initial position estimate. The initial position estimate may contain, for example, information about both the location and the orientation of the object. An updated position estimate is calculated by comparing the initial image with a template image of the object. The template image depicts a synthesized projection image of the object positioned in the medical imaging system at a position estimate that is in a neighborhood about the selected initial position estimate. An image is reconstructed from the acquired image data, and a refined position estimate is calculated by comparing this reconstructed image with an updated template image. The updated template image depicts a synthesized projection image of the object positioned in the medical imaging system at the updated position estimate. From the refined position estimate, the three-dimensional location of the object can be determined.

It is another aspect of the invention to provide a method for determining a three-dimensional location of an interventional medical device using a two-dimensional x-ray image obtained with an x-ray imaging system. The method includes acquiring x-ray image data with the x-ray imaging system, reconstructing an initial image from down-sampled image data produced by down-sampling the acquired x-ray image data by a down-sampling factor, and reconstructing an image from the acquired x-ray image data. An initial position estimate of the medical device is determined and updated by iteratively calculating a shift-invariant similarity measure between the initial image and a template image. The template image depicts a synthesized x-ray projection of the medical device positioned at the initial position estimate. The initial position estimate and template image are updated in successive iterations and the shift-invariant similarity measure is iteratively calculated until the shift-invariant similarity measure exceeds a threshold value. The updated position estimate is then refined by iteratively calculating a shift-variant similarity measure between the reconstructed image and a template image. The template image depicts a synthesized x-ray projection of the medical device positioned at the updated position estimate. The updated position estimate and template image are updated in successive iterations and the shift-variant similarity measure is iteratively calculated until the shift-variant similarity measure exceeds a threshold value. From the refined position estimate, the three-dimensional location of the medical device may be determined.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
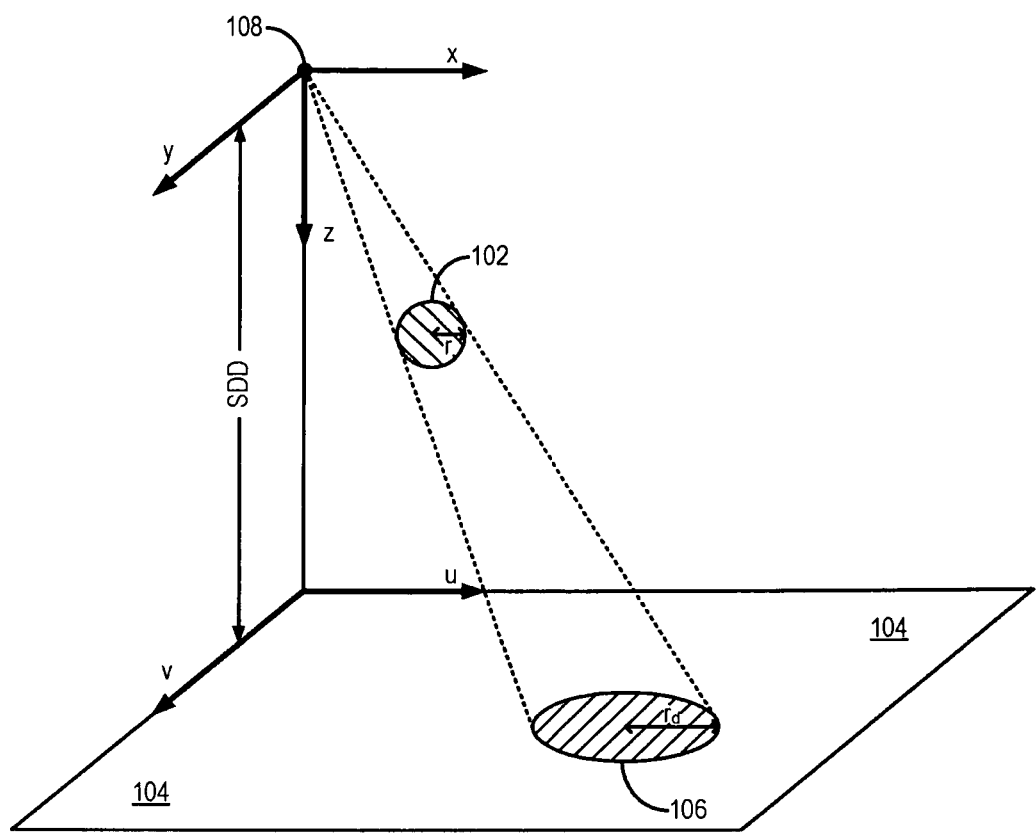
FIG. 1 is a pictorial illustration of an example of an x-ray imaging system geometry and the magnification of a spherical marker imaged with such an x-ray imaging system.

A method for three-dimensional localization of an interventional medical device, a portion thereof, or a marker disposed thereon is provided. The localization is performed on a two-dimensional image, such as a two-dimensional image obtained with an x-ray imaging system, such as an x-ray C-arm imaging system. The provided method allows for a cost reduction in the performance of interventional cardiology procedures, as compared to other expensive alternatives for localization that are currently available in market. In addition, the method may also provide a significant reduction in x-ray radiation imparted to a patient during an interventional procedure. The method for localization combines sensitivity with the robustness necessary to measure the three-dimensional position of an interventional medical device from a single-plane fluoroscopic image in real time. As referred to herein, the term "position" is used to refer to both a location and an orientation. For example, the position of an object includes both the location of that object in space, and also its orientation. The location of an object in space may be defined using three spatial-location variables, such as (x,y,z) coordinates, and the orientation of an object in space may be defined using rotation angles, which may be Euler angles ($\theta,\phi,\eta$).

Generally, the proposed method for determining the position of an object from a two-dimensional x-ray image can be summarized as follows. A two-dimensional cone beam projection of an x-ray object model located at ($x_0$, $y_0$, $z_0$) with an orientation specified by three Euler angles ($\theta,\phi,\eta$) is computed, yielding a synthetic x-ray projection of the object referred to as a "template image." Simulated x-ray projections of an object can be calculated for different locations and orientations of the object by translating and rotating the combination of the x-ray source and x-ray detector. It is possible to specify the x-ray source position using object centric spherical coordinates ($\theta,\phi$) and to specify the rotation of the detector about a vector normal to the detector plane by the angle $\eta$. Rotation about this arbitrary axis can be computed using quaternions, which provide both conceptual and numerical advantages for describing the acquisition geometry, and any changes thereof. As used in the succeeding description, the object may be a marker, an interventional medical device, or a portion of an interventional medical device. Examples of interventional medical devices include catheters, such as electrophysiology catheters and ablation catheters. Examples of markers that may be used include spherical markers; however, markers with other geometries may also be used. It is noted that orientation cannot be reliably estimated from a single spherical marker alone; rather, when using a spherical marker, additional markers or the object itself should be included in the template model in order to obtain a reliable measurement of the orientation of the object. Template matching is used to obtain a measure of similarity between the template image and the object found in the x-ray image. Multi-dimensional optimization using the measure of similarity determines the optimum values of ($x_0$, $y_0, z_0, \theta, \phi, \eta$) resulting in the best match with a model of the object.

By way of example, FIG. 1 illustrates how an x-ray image may be viewed as a magnified projection of a three-dimensional object, such as a spherical marker 102. In FIG. 1, SDD is the source-to-detector distance, and (u,v) is a coordinate system on the x-ray detector 104, whose origin corresponds to the central axis of the x-ray beam. The spherical marker 102 is located at coordinates (x,y,z), and yields a magnified image 106 of the spherical marker 102 on the detector 104. The relative errors in x, y, and z are determined mostly by errors in estimating the magnification, which results in larger errors in the z-direction. In this configuration, the magnification, M, of the spherical marker 102 is given as the ratio of the radius, $r_d$, of the magnified image 106 to the radius, r, of the spherical marker 102:

$$M = \frac{r_d}{r}. \tag{1}$$

Thus, the following relationships exist between the coordinates in the x-ray detector 104 and the spatial coordinates (x,y,z):

$$x = \frac{u}{M}; \quad (2)$$

$$y = \frac{v}{M}; \quad (3)$$

$$z = \frac{SDD}{M}. \quad (4)$$

Figure 2:
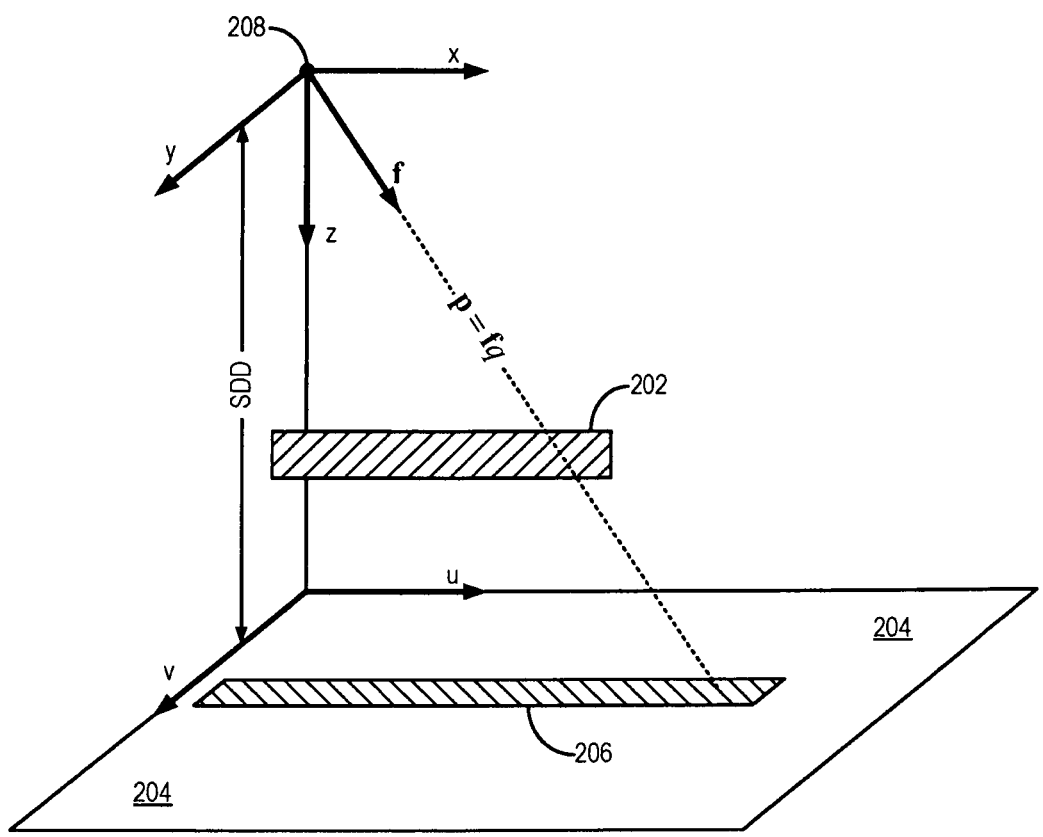
FIG. 2 is a pictorial illustration of an example of an x-ray imaging system geometry and the magnification of an object imaged with such an x-ray imaging system.

By way of another example, FIG. 2 illustrates how an x-ray image may be viewed as a magnified projection of a three-dimensional object. The object 202 shown in FIG. 2 may be, for example, computed from a microCT reconstruction of the object. In FIG. 2, SDD is the source-to-detector distance, and (u,v) is a coordinate system on the x-ray detector 204, whose origin corresponds to the central axis of the x-ray beam. The object 202 is located at coordinates (x,y,z), and yields a magnified image 206 of the object 202 on the detector 204. The relative errors in x, y, and z are determined mostly by errors in estimating the magnification, which results in larger errors in the z-direction. For a complex object, such as an interventional medical device, the projection image will depend on the orientation of the object 202, and different parts of the object 202 will be magnified by different amounts.

The aforementioned concept of magnification is useful for understanding the principle behind localization, but this measure is of limited use in localizing an object with the desired accuracy. The method for localization provided herein relies instead on computing a synthetic x-ray projection of a three-dimensional model of the object-of-interest and varying its location and orientation until it resembles the projection of the actual object in the x-ray image. In order to determine the position of an object within a few millimeters using an x-ray catheterization system, it is necessary to be able to detect sub-pixel changes in the extent of the projection of the object. Preferably, the object will have a high contrast-to-noise ratio to more readily facilitate the detection of such sub-pixel changes.

As mentioned above, the present invention makes use of template images that are synthetic x-ray projection images of the object to be localized. Let (x,y,z) specify a location in an x-ray source and detector centric coordinate system, such as those illustrated in FIGS. 1 and 2. In such a coordinate system, the x-ray source is located at coordinates (0,0,0) and the detector plane is located at z=SDD, where SDD is again the source-to-detector distance. A point on the detector is given by the coordinates (u,v), where u and v are respectively along the same directions as x and y. Furthermore, let $\mu(p', E)$ represent an x-ray object model describing x-ray attenuation properties at a point, $p'=(x,y,z)$, as a function of x-ray energy, E=hv. The x-ray attenuation coefficient for a material can be calculated from tables when the chemical composition and density of that material are known or estimated from computed tomography reconstructions that have been calibrated to Hounsfield units.

The x-ray object model can be shifted by an amount, $\Delta=(x_0, y_0, z_0)$, and oriented by the angles $(\theta,\phi,\eta)$ such that:

$$p = Rp' + \begin{pmatrix} x_0 \\ y_0 \\ z_0 \end{pmatrix}; \quad (5)$$

where:

$$R = \begin{pmatrix} \cos\phi & \sin\phi & 0 \\ -\sin\phi & \cos\phi & 0 \\ 0 & 0 & 1 \end{pmatrix} \begin{pmatrix} \cos\theta & 0 & \sin\theta \\ 0 & 1 & 0 \\ -\sin\theta & 0 & \cos\theta \end{pmatrix} \begin{pmatrix} 1 & 0 & 0 \\ 0 & \cos\eta & \sin\eta \\ 0 & -\sin\eta & \cos\eta \end{pmatrix}. \quad (6)$$

Attenuation of x-rays occurs between the x-ray source and a detector pixel at location (u,v) along a line given by:

$$p = fq \quad (7);$$

where q is a scalar parameter that controls motion along the line and f is a vector having the form:

$$f = (1,0,0)u + (0,1,0)v + (0,0,SDD) \quad (8).$$

Let $\psi(E)$ describe the energy fluence of x-rays reaching the object as a function of photon energy, E=hv. This function depends on x-ray acquisition parameters, such as kVp, tube current, and beam filtration. Models exist to approximate this function. These acquisition parameter values are available for some catheterization systems in real-time; however, they may also be estimated based on average characteristics for the object.

The signal due to primary radiation absorbed by an object at the location (u,v) and recorded at the detector is given by the path integral:

$$P(u, v) = \int \Psi(E) \exp\left(-\int \mu\left(\frac{f}{\|f\|}q, E\right) dq\right) dE. \quad (9)$$

Eqn. (9) may be discretized by replacing the integrals with summations over energy and distance controlled via the scalar parameter, q.

For x-ray attenuating objects that are small relative to the x-ray source distance, the rays, f, given by Eqn. (9) that are touching the object are essentially parallel and can, therefore, be computed via the central slice theorem. Using this approach, a three-dimensional fast Fourier transform ("3D FFT") of the x-ray object model is computed. All projections of the x-ray model can subsequently be computed by interpolating the complex 3D FFT data onto a complex plane whose normal is parallel to f, and by performing an inverse 2D FFT of said plane. Finally, the object may be scaled to simulate magnification of the object. This approach can be used to speed up calculation in Stage 1 and also in the first iterations of Stage 2, as identified below.

For objects that are composed of a limited number of materials, such as many interventional medical devices, the object can be represented as a solid parametric model that describes only material boundaries. Using such a model, x-ray attenuations can be calculated quickly because these calculations are reduced to determining path lengths through each material. The determination of the path length through one material requires only the determination of the entry point and exit point of a ray at the material boundary. This approach is suitable for calculating x-ray attenuations in both Stage 1 and Stage 2.

In order to more closely simulate the attenuation of x-rays in the patient, an additional patient equivalent attenuation component can be added whose thickness is provided by some catheterization system or via assumptions made for an average patient.

X-ray interactions within the patient generate scattered radiation whereby photons having degraded positional information also reach the detector. Scattered radiation can be treated to the first order as a blurred version of the primary radiation signal, whose intensity depends on x-ray technique factors and patient-source-detector geometry. Generally, a small object, such as a marker disposed on a medical device, has a minimal impact on the scattered radiation field. Thus, scatter over the small area in the vicinity of the marker can be treated as an added uniform background signal, to which the similarity measure proposed below is insensitive.

To generate a template image, T'(u,v,g), that describes the resulting signal at each pixel on the x-ray detector, where $g=(x_0,y_0,z_0,\theta,\phi,\eta)$ is a vector that contains the geometry variables specifying the location and orientation of the object model, Eqn. (9) is used. The geometry variables are varied as a part of the localization, as will be described below. The template image may also depend on numerous x-ray acquisition parameters, which are omitted for notational simplicity.

Images are generally represented as two dimensional rectangular arrays of pixels. The projection of an object onto an image is not generally rectangular and, thus, only a subset of pixels will be associated with the object. In a clinical image, pixels in the periphery of the object projection are associated with anatomical structures and these pixels, if included in a template matching calculation, would add variability to the position estimates. Thus, in order to exclude these peripheral pixels, the template images may be masked. A suitable mask function for this purpose is defined as follows:

$$M(u, v, g) = \begin{cases} 1 & \text{if the line } p = fq \text{ touches the object} \\ 0 & \text{otherwise} \end{cases} \quad (10)$$

The mask may be defined to include a few pixels just beyond the edge of the object, which may be referred to as a halo region because it results in the appearance of a bright border in the template image. These additional pixels beyond the edge of the object reduce the bias in estimating the radius of the object in the presence of image blurring due to the x-ray detector and x-ray focal spot. These enlarged boundaries can be created using, for example, region growing techniques. The mask function is subsequently applied to the template image to produce a masked template image:

$$T''(u,v,g)=T(u,v,g)M(u,v,g) \quad (11).$$

The template image may also be further modified to have a zero mean, such that:

$$T(u, v, g) = \begin{cases} 0 & \text{for } M(u, v, g) = 0 \\ T''(u, v, g) - S(g) & \text{for } M(u, v, g) \neq 0 \end{cases} \quad (12)$$

where:

$$S(g) = \sum_{u,v} \frac{T''(u, v, g)}{M(u, v, g)}. \quad (13)$$

The mean may be removed from the template image so it does not have to be subtracted in the subsequent template matching calculation described below.

Blurring of the object may occur as a result of the finite size of the focal spot and as a result of other detector blurring effects. This blurring varies as a function of the object distance from the focal spot, which may cause a varying systematic error in estimated object position. Given an x-ray focal spot distribution and x-ray detector transfer function, a blurring kernel for the x-ray image can be estimated and convolved with the template image to match the blurring found in the x-ray image, thereby reducing these systematic errors.

After template images of the object have been generated, they are used to localize the three-dimensional positional information of an object in two-dimensional images of a patient undergoing an interventional procedure.

In general, the provided method for three-dimensional localization of an object in a two-dimensional image is designed to detect sub-pixel changes in the geometry of the object in the acquired image. Template images of the object are computed with different geometries that correspond to different magnifications or orientations of the object. Preferably, these template images are previously calculated and stored for use during a real-time localization process. A rough estimate of the position and size of object is obtained from a down-sampled image, such as one that is down-sampled by a factor of four. This matching step is robust to changes in background signal in the vicinity of the object, to penetrating power of the x-ray beam, and to changes in x-ray attenuation over different parts of the patient's anatomy, which would otherwise lead to spatial variation in the position estimates.

Localization of a non-spherical object requires the computation of x-ray projections for different positions of the object model. Rotation and translation of this model is computationally expensive; thus, it is advantageous to instead compute the various projections for different positions of the x-ray source as well as different positions of the detector. These various geometries can equivalently be described as rotation of the source and detector in tandem specified by Euler angles ($\theta,\phi,\eta$) about the point ($x_0,y_0,z_0$). It is convenient to select the axis of rotation to be a point, ($x_0, y_0, z_0$), located within the object model so that rotations do not cause large shifts in the projection of the model onto the simulated detector. Thus, the parametric line equation, such as the one in Eqn. (7), is transformed such that:

$$p' = Rp - \begin{pmatrix} x_0 \\ y_0 \\ z_0 \end{pmatrix}; \quad (14)$$

where R is the rotation matrix defined above in Eqn. (6).

Figure 3:
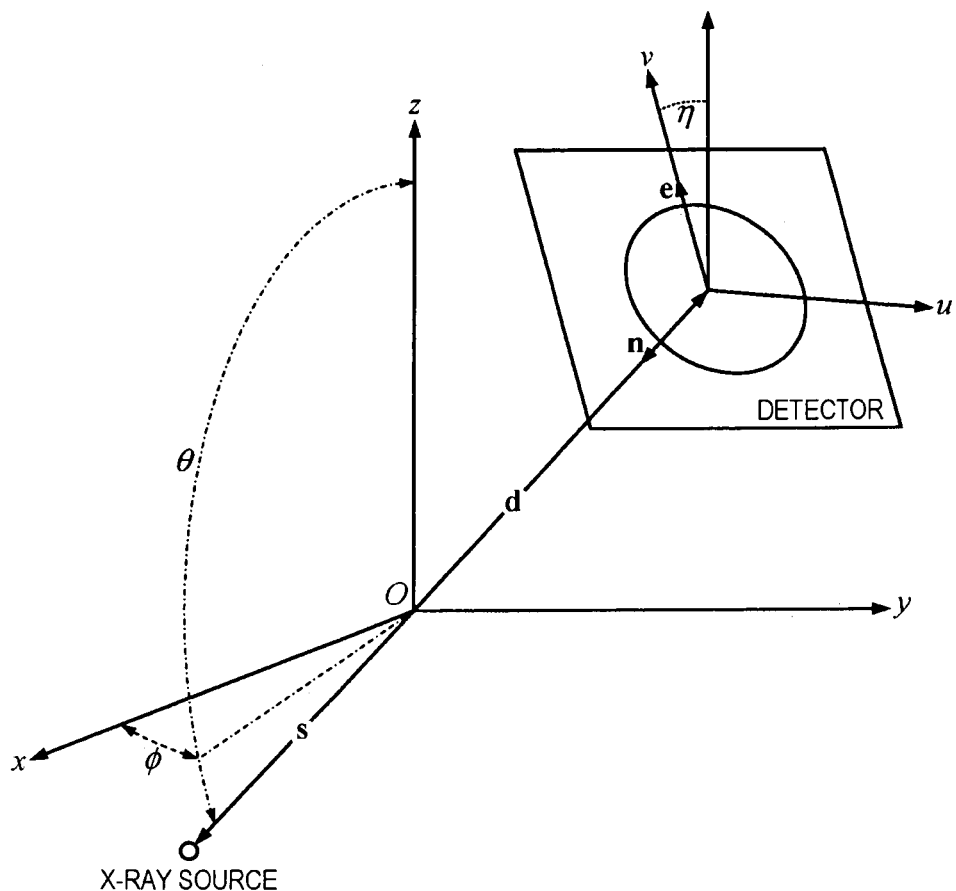
FIG. 3 is a pictorial representation of an x-ray acquisition geometry in which the x-ray source coordinates are specified by spherical angle coordinates ($\theta$, $\phi$) and the x-ray detector rotation is specified by an angle $\eta$.

The preceding formulation provides the degrees of freedom necessary to simulate changes in object position. Unfortunately, it is not intuitive to visualize Euler angle combinations that yield a projection of the object with the desired appearance. Instead, the acquisition geometry is better described as the rotation of the x-ray source and x-ray detector in tandem about the origin of coordinates, as depicted in FIG. 3, where n is a vector normal to the detector, e is a vector oriented along the v-edge of the detector, d is a vector describing the origin-to-detector distance, and s is a vector describing the origin-to-source distance. Thus, a location (u,v) on the detector corresponds to:

$$(x,y,z)=d+u*e+v e \times n \quad (15).$$

In a restricted isocentric rotation geometry, the source position can be described by the spherical coordinates $\theta$ (co-elevation) and $\phi$ (azimuth) such that:

$$s=\|s\|n \quad (16);$$

where:

$$n=(n_x,n_y,n_z)=(\sin\theta\cos\phi,\sin\theta\sin\phi,\cos\theta) \quad (17);$$

and the detector position is given by:

$$d = -\|d\|n \quad (18)$$

In order to produce all possible acquisition geometries, the detector should be allowed to rotate about its central axis by an angle, $\eta$, about the n-axis. Rotation about such an arbitrary axis may be achieved using quaternions applied to the detector vector, e, which yields:

$$e' = QeQ^*; \quad (19)$$

where:

$$Q = \left(\cos\left(\frac{\eta}{2}\right) + \hat{i}n_x\sin\left(\frac{\eta}{2}\right) + \hat{j}\sin\left(\frac{\eta}{2}\right) + \hat{k}\sin\left(\frac{\eta}{2}\right)\right). \quad (20)$$

Figures 4A, 4B, 4C:
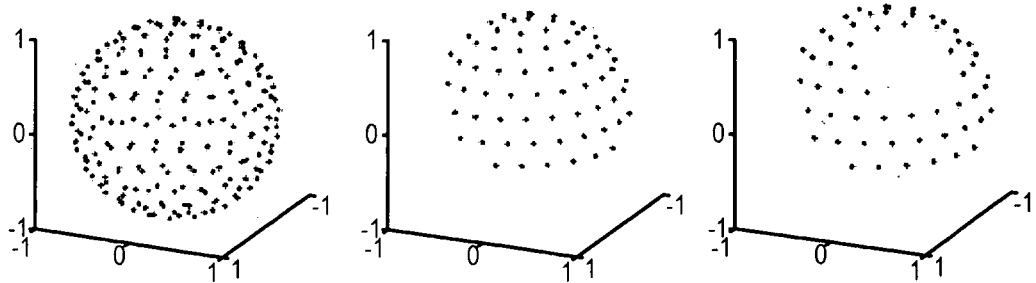
FIGS. 4A-C are examples of x-ray source positions that are uniformly distributed on the surface of a sphere or a portion thereof.

It is advantageous, in terms of computational efficiency, to generate x-ray source positions that are uniformly distributed on a subset of a sphere. This allows the avoidance of undersampling or oversampling orientations along particular source directions. Methods for calculating such a distribution of points on a sphere are described, for example, by E. A. Rakhmanov, et al., in "Minimal Discrete Energy on the Sphere," *Math. Res. Lett.,* 1994; 1(6):647-662, and by E. B. Saff and A. B. J. Kuijlaars in "Distributing Many Points on a Sphere," *The Mathematical Intelligencer,* 1997; 19(1):5-11. FIG. 4A illustrates an example of two hundred points generated uniformly around a sphere using such methods. FIG. 4B shows an example of a subset of these points, in which the points are restricted to a maximum cone angle (relative to the origin of the coordinate space), $\alpha_{max}$, about an arbitrary direction. In FIG. 4C, the points are limited to lie between the maximum and minimum cone angles, $\alpha_{min}$ and $\alpha_{max}$, respectively. These restrictions reduce the number of directions used in determining the object orientation, thereby speeding up calculations when analyzing a sequence of images acquired in succession. Finally, it is noted that these orientations are transformed back into the detector-source centric x-ray coordinate system.

Figure 5A:
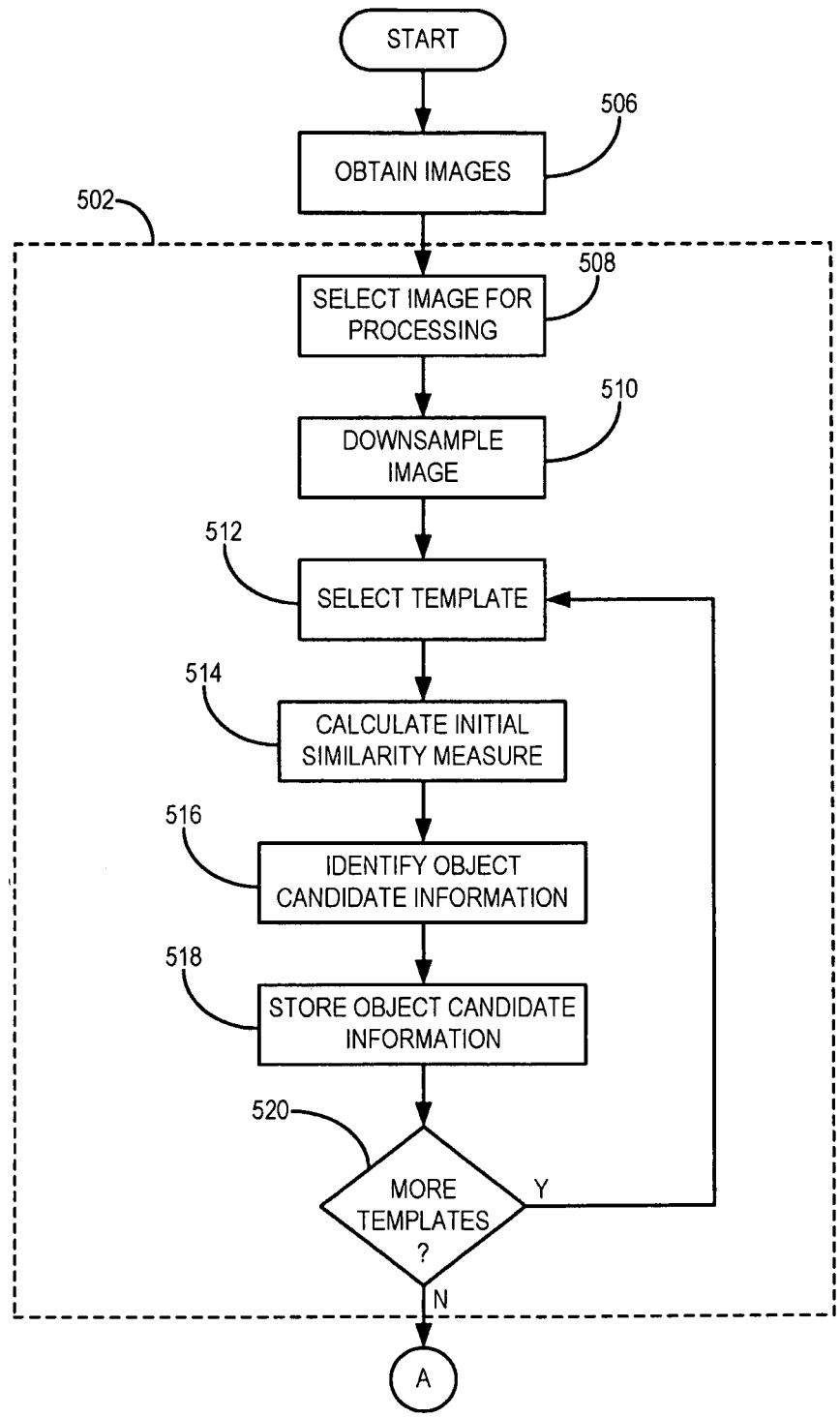
FIGS. 5A and 5B are a flowchart setting forth the steps of an example of a method for localizing an object in three-dimensional space from a two-dimensional image depicting the object.
Figure 5B:
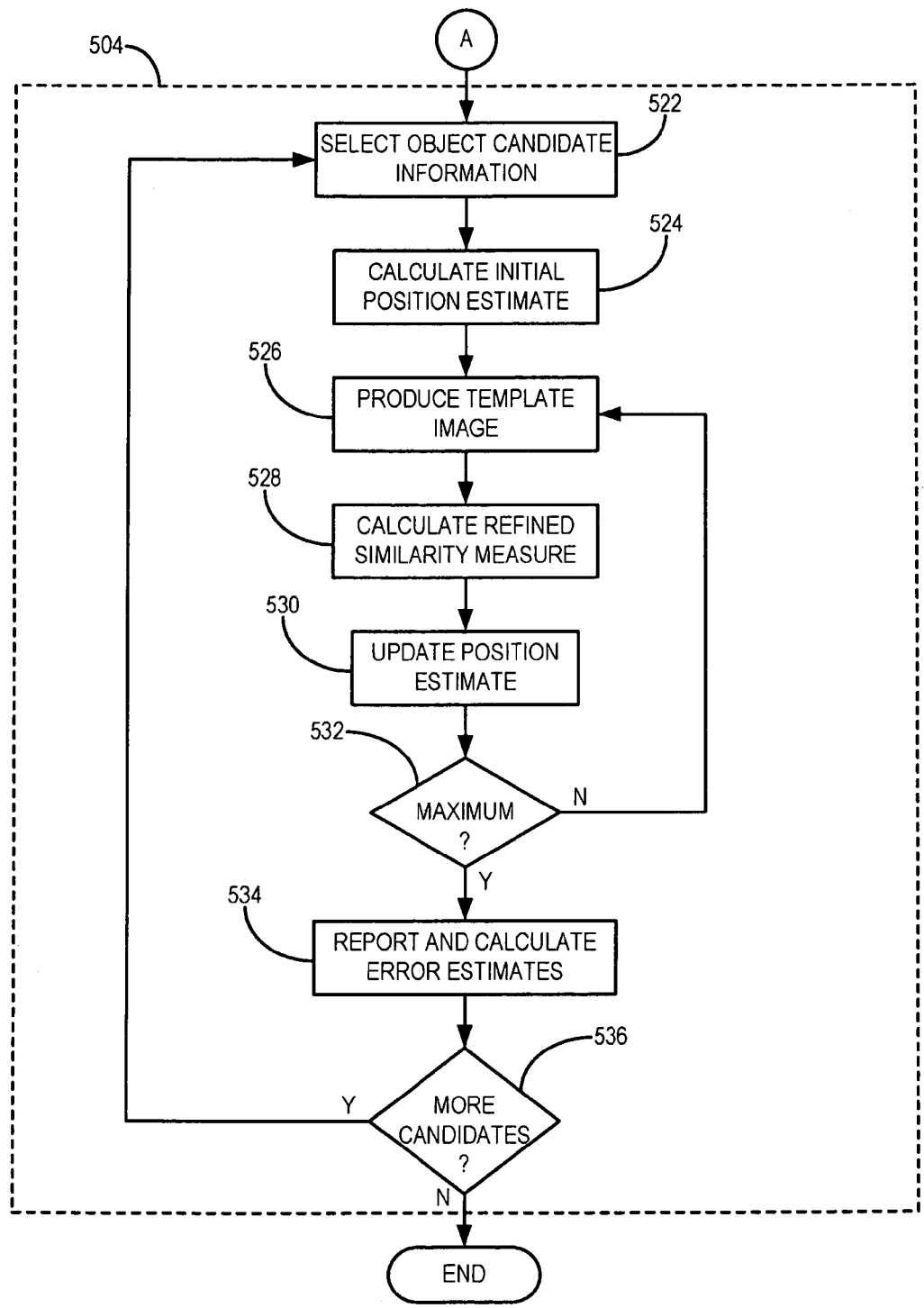

Referring now to FIGS. 5A and 5B, a flowchart setting forth the steps of an example of a method for three-dimensional localization of an object depicted in a two-dimensional image is illustrated. The method generally includes two stages: a first stage 502, and a second stage 504. The method begins by obtaining images with a medical imaging system, such as the acquisition of x-ray images with a C-arm x-ray imaging system, as indicated at step 506. The first stage 502 of the method then begins with the selection of an image to be processed, as indicated at step 508. This selected image is then down-sampled, as indicated at step 510, so that an initial estimate of the position of the object to be localized can be quickly established. By way of example, the selected image may be down-sampled by a factor of four.

One of a plurality of stored template images is initially selected for comparison with the down-sampled image, as indicated at step 512. The down-sampled image is then compared with the selected stored template image in order to produce an initial measure of the similarity between the down-sampled image and the template image, as indicated at step 514. By way of example, the comparison is performed using a normalized cross-correlation, as will be described below in detail. Accordingly, the measure of similarity may include a normalized cross-correlation map for the template image. Object candidate information is subsequently identified using the calculated similarity measure, as indicated at step 516, and this information is stored for later use, as indicated at step 518. A determination is then made at decision block 520 whether all of the desired stored template images have been compared with the down-sampled image. If not, then another template image is selected and steps 514-518 are repeated for that template image. When all of the desired template images have been compared with the down-sampled image, the method proceeds to the second stage 504. By way of example, the down-sampled image may be compared to a limited number of template images for computational efficiency.

An example of producing a normalized cross-correlation ("NCC") map is now provided. The target image, $I(u,v)$, such as the initial image, is defined as having $M_1 \times N_1$ pixels, such that $I(u,v)=0$ for $u<0$ or $u \geq M_1$, or for $v<0$ or $v \geq N_1$. Similarly, the template image, $T(u,v,g)$ has $M_T \times N_T$ pixels, such that $T(u,v,g)=0$ for $u<0$ or $u \geq M_T$, or for $v<0$ or $v \geq N_T$. The NCC of the target image and template image is given by:

$$C_1(u, v, g) = \frac{\sum_{u'}\sum_{v'} I(u', v', g)(T(u'-u, v'-v, g) - \overline{T(g)})}{\sqrt{\sigma_I^2(u, v, g)\sigma_T^2(g)}}; \quad (21)$$

where:

$$\sigma_I^2(u, v) = \sum_{u'=u}^{u+M_T-1}\sum_{v'=v}^{v+N_T-1}(I(u', v') - \overline{I(u, v)})^2; \quad (22)$$

$$\sigma_T^2(g) = \sum_{u'}\sum_{v'}(T(u', v', g) - \overline{T(g)})^2; \quad (23)$$

$$\overline{I(u, v)} = \sum_{u'=u}^{u+M_T-1}\sum_{v'=v}^{v+N_T-1}\frac{I(u', v')}{N_T M_T}; \quad (24)$$

and $$\overline{T(g)} = \sum_{u'}\sum_{v'}\frac{T(u', v', g)}{N_T M_T}. \quad (25)$$

The NCC is a measure of how well the template shifted by $(u,v)$ resembles the target image. The position corresponding to a good match is obtained by noting the shift values, u and v, that yield a peak value in $C(u,v,g)$. It can be shown that the NCC provides a measure of similarity between the template signal and the target signal that is independent of changes in signal scaling or signal offset, with $C_1 \in [-1.0, 1.0]$. If the target image is given by:

$$I(u,v)=aT(u-u_0,v-v_0)+b \quad (26);$$

then the NCC operation between $I(u,v)$ and $T(u,v)$ would yield maximum for $C_1$ at $(u_0,v_0)$ such that $C_1(u_0,v_0)=1.0$ independent of a and b. By way of example, the template image, $T(u,v)$, may be constructed to have a mean value of zero upon generation, making the subtraction of the mean shown in Eqn. (24) redundant in these instances.

Calculation of NCC by way of Eqn. (21) is computationally intensive due to the correlation operation in the numerator and the term $\sigma_1^2(u,v,g)$ in the denominator, which must both be recomputed for each template shift, $(u,v)$. A search for an object in an image requires the computation of $C_1(u,v,g)$ for numerous shift values, $(u,v)$, and is impractical using Eqn. (21) for real-time applications. This drawback can be overcome by computing $C_1(u,v,g)$ for a plurality of equally spaced values in $(u,v)$ using a fast Fourier transform ("FFT") for the correlation operation. In addition, the term, $\sigma_1^2(u,v,g)$, can be computed more efficiently for a plurality of $(u,v)$ values using sum tables.

Sum tables allow the rapid recalculation of operations on pixels constrained within a moving rectangular sub-region of an image: This sub-region can also be thought of as a rectangular mask or window applied to the image. If an arbitrarily shaped mask function, such as the mask function M(u,v,g) defined above, is used to limit the correlation calculation to the object in the template, the mask function should be decomposed into a series of rectangles to efficiently limit the calculation of $\sigma_1^2(u,v,g)$ to the same subset of image pixels using sum tables. By way of example, the mask function may be decomposed as stated using the method described by S. Wu and S. Sahni in "Fast Algorithms To Partition Simple Rectilinear Polygons," *VLSI Design*, 1994; 1(3):193-215. It is noted that the coarseness of the rectangles may be increased to limit their number.

Referring again to FIGS. 5A and 5B, after the object candidate information, such as the initial estimate of the position of the object, is made stored at step 516, and after it has been determined at decision block 520 that all of the desired template images have been processed, an optimization is performed to refine the estimated position information of the object. First, one of the stored sets of object candidate information is selected for processing, as indicated at step 522. Using this stored object candidate information, an initial position estimate of the object is calculated, as indicated at step 524, using the following equations:

$$M = \frac{SDD}{z}; \qquad (27)$$

$$(x, y, z) = \left(\frac{u}{M}, \frac{v}{M}, \frac{SDD}{M}\right). \qquad (28)$$

As indicated at step 526, the initial position estimate is then used to produce a template image for comparison with the non-down-sampled image initially selected at step 508. A refined similarity measure is then calculated between the produced template image and the initially obtained, non-down-sampled image, as indicated at step 528. An example of the refined similarity measure is a so-called normalized similarity integral. The NCC in Eqns. (21)-(25) is expressed with double sums over the variables u and v. However, if the NCC calculation is performed for an arbitrary subset of template pixels specified by a mask function, the pixels for which M(u,v,g)≠0 can be made into a list $(u_k,v_k)$ for k∈[1,K] such that:

$$C_2 = \frac{\sum_k I(u_k, v_k)(T(u_k, v_k, g) - \overline{T(g)})}{\sqrt{\sigma_I^2(g)\sigma_T^2(g)}}; \qquad (29)$$

where $$\sigma_I^2(g) = \sum_k (I(u_k, v_k) - \overline{I(g)})^2; \qquad (30)$$

$$\sigma_T^2(g) = \sum_k (T(u_k, v_k, g) - \overline{T(g)})^2; \qquad (31)$$

$$\overline{I(g)} = \sum_k \frac{I(u_k, v_k)}{K}; \qquad (32)$$

and $$\overline{T(g)} = \sum_k \frac{T(u_k, v_k, g)}{K}. \qquad (33)$$

Eqn. (29) is not a correlation operation because the template is not shift invariant; thus, the measure of similarity provided by Eqn. (29) is referred to as a normalized similarity integral ("NSI") instead. The NSI yields a value of one if there is a perfect match between the x-ray image and template image within a scaling factor and offset, as was the case with the NCC. In Eqns. (30) and (32), a dependency on the geometry, g, is added to underscore the fact that the list of pixels included in the calculation is geometry dependent and changes with g.

As indicated at step 530, the calculated refined similarity measure is used to update the position estimate of the object. As will be described in some detail, the refined similarity measure is iteratively calculated using an optimization technique, thereby providing an iterative updating of the position estimate until a suitable stopping criterion is satisfied. A determination is therefore made at decision block 532 whether the updated position estimate results in a similarity measure that satisfies a stopping criterion. If not, then the updated position estimate is used to produce an updated template image at step 526, and steps 528-530 are repeated. If the stopping criterion is satisfied, then the updated position estimate is stored as the location of the object, which may then be reported along with error estimates, as indicated at step 534. A determination may then be made as to whether additional object candidate information should be processed, as indicated at step 536. If such additional processing is desired, then steps 522-534 may be repeated.

By way of example, a simplex method or a Broyden-Fletcher-Goldfarb-Shannon ("BFGS") method may be used to perform the aforementioned minimization of the refined similarity measure. The BFGS approach is considered to be more efficient in terms of the number of iterations, but it is contemplated that the simplex method may provide more accurate results in general. During this minimization, values of $C_2(g)$ are computed for discrete values of g for each iteration of the optimization algorithm, and these values are not selected a priori because they are "driven" by the optimization technique. The refined maxima $C_2(g) > C_{2,min}$ are retained yielding values of $\hat{g}$ for m∈[1, ..., M], representing the final estimate for the location of the object in the reconstructed image. The value of $C_{2,min}$ may be determined experimentally. The number of object candidates that are retained can also be adjusted to match the number of objects known to be in the field of view.

Real-time x-ray imaging is a dynamic process where changes in x-ray transmission due to respiratory and cardiac motion as well as gantry motion cause changes in x-ray transmission through the patient. These x-ray transmission changes are compensated by changes in kVp, filtration, and tube current. The NCC and NSI measures are advantageous for detecting objects in x-ray images due to their insensitivity to signal level and gain; however, in some circumstances, a low contrast feature that is not the object may generate a peak in the similarity measure of greater value than the object, possibly resulting in a false positive detection of the object. Some spurious peaks in the similarity measure related to such a scenario can be disregarded by introducing additional penalties described below. These penalties may be expressed as multiplicative terms, $P_j$, with values $P_j \leq 1.0$ such that:

$$C'(\hat{u}_m, \hat{v}_m, \hat{g}_n) = C(\hat{u}_m, \hat{v}_m, \hat{g}_n) \prod_j P_j; \qquad (34)$$

where C may be the NCC or NSI measure.

A first example of a penalty term is a motion penalty term that may be defined as:

$$P_m(x_{f+1}, y_{f+1}, z_{f+1}, x_f, y_f, z_f) = \qquad (35)$$
$$\exp\left(-\frac{(x_{f+1} - x_f)^2 + (y_{f+1} - y_f)^2 + (y_{f+1} - y_f)^2}{2\sigma_m^2(t_{f+1} - t_f)^2}\right);$$

where f is the frame number in a sequential acquisition of images normalized by the time difference between successive frames. Eqn. (35) creates a penalty when the marker velocity is comparable or greater than $\sigma_m$.

A second example of a penalty term is an object orientation penalty term, which may be defined as:

$$P_o(\theta_{f+1}, \phi_{f+1}, \eta_{f+1}, \theta_f, \phi_f, \eta_f) = \qquad (36)$$
$$\exp\left(-\frac{(\theta_{f+1} - \theta_f)^2 + (\phi_{f+1} - \phi_f)^2 + (\eta_{f+1} - \eta_f)^2}{2\sigma_o^2(t_{f+1} - t_f)^2}\right);$$

where f is the frame number in a sequential acquisition of images normalized by the time difference between successive frames. Eqn. (36) creates a penalty when the change in object orientation is comparable or greater than $\sigma_o$.

A third example of a penalty term is a contrast penalty term. The relationship between the x-ray energy deposited at a pixel location and the digitized pixel value can generally be established within a scaling factor. The scaling factor depends on amplifier settings, which the system may change depending on acquisition conditions. The contrast of an object is independent of this scaling factor, and can be predicted via a model of x-ray interactions in the patient, as described in Eqn. (9). The contrast represents an additional constraint that can be used to exclude spurious maxima in the NCC and NSI measures.

A measure of contrast of the object in the image can be defined from components already computed as part of the NCC calculation. By way of example, a measure of image contrast can be given as:

$$CO_I = \frac{\sigma_I(g)}{I(g)}; \qquad (37)$$

for the object found at location (u,v), and a measure of template image contrast can be given as:

$$CO_T = \frac{\sigma_T(g)}{S(g)}. \qquad (38)$$

Accordingly, a contrast penalty may be written as:

$$P_C(CO_I, CO_T) = \exp\left(-\frac{(CO_I - CO_T)^2}{2\sigma_{CO}^2}\right); \qquad (39)$$

where $\sigma_{CO}$ is determined experimentally.

Object locations typically change little from one x-ray frame to the next due to the high rate of image acquisition; therefore, the exhaustive search for the object in Stage 1 performed by calculating the NCC using many templates can be accelerated. The range of orientation and location of the object can be restricted, thereby reducing the number of templates used and restricting the template search to a subset of the image.

Both the NCC and NSI measures provide a measure of similarity of the template to the matched feature in the processed image, and these measures can be calibrated to provide error estimates of the position. The computed position of the template using the aforementioned method allows the superposition of the template model onto the projection image using, for example, image fusion techniques. By superimposing the template onto the projection image, an operator can visually inspect the overlap to provide a visual estimate of the quality of the computed position.

The position estimates are obtained in an x-ray source and x-ray detector centric system. If any of the x-ray system components move relative to the object being imaged, previously obtained positions should be transformed to the current coordinate system if they are to be used with the current images. Alternatively, all of the calculated positions can be transformed into the same x-ray object centric or laboratory centric coordinate system. The aforementioned coordinate system transformation can be determined from sensors that record x-ray geometrical parameters including, but not limited to, table motion and gantry geometrical parameters. Examples of gantry geometrical parameters include C-arm rotation parameters and x-ray source-to-detector distance. By way of example, some or all of the aforementioned parameters may be available in real-time from a computer controlling the x-ray systems. Also by way of example, some or all of the aforementioned geometrical parameters can be obtained by using a position measurement system to measure the position of components of the x-ray, such as a position measurement system based on the detection of passive markers that reflect infra red light or active markers that emit infra red light.

The imaging volume may also contain additional x-ray attenuating markers, which can be localized using the provided method for x-ray localization. Such markers allow the detection of the motion of structures supporting the object being imaged relative to the x-ray source and detector. For example, these markers can be used to detect table motion and gantry rotation. The positions of these markers can also be used towards the computation of the coordinate system transformation described above.

Figure 6A:
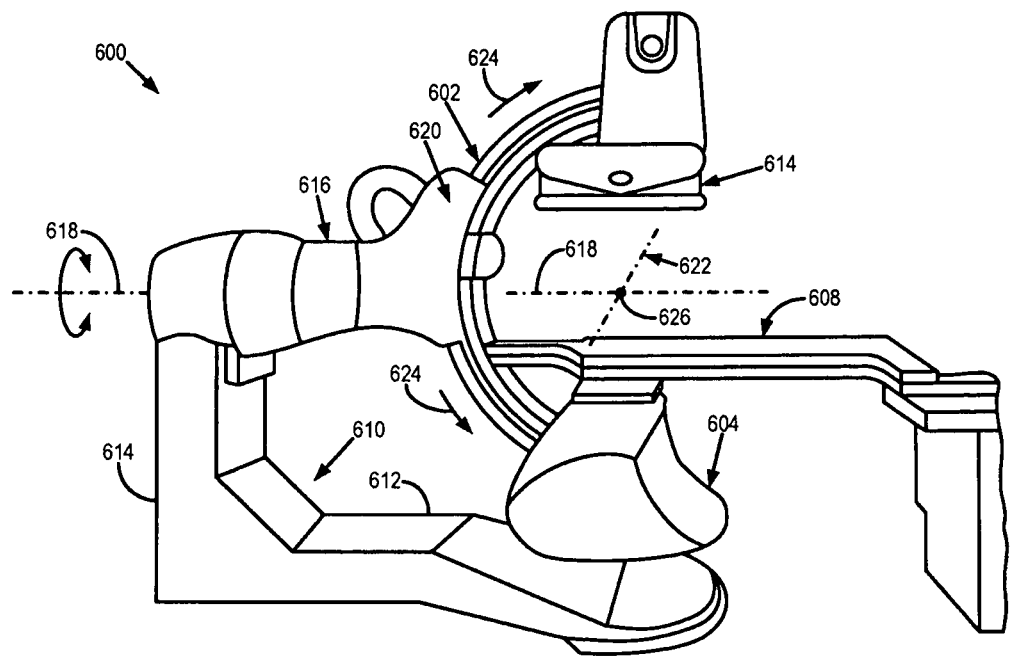
FIG. 6A is a pictorial view of an example of a C-arm x-ray imaging system.
Figure 6B:
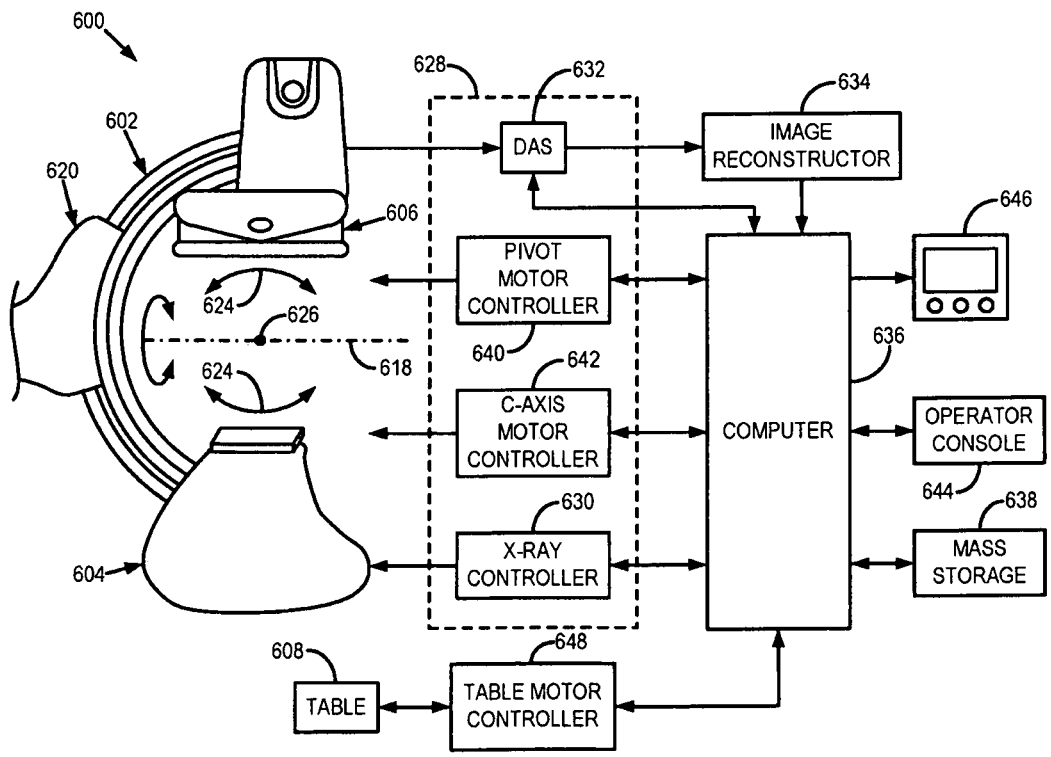
FIG. 6B is a block diagram of the C-arm x-ray imaging system of FIG. 6A.

Referring particularly to FIGS. 6A and 6B, an example of a so-called "C-arm" x-ray imaging system 600 is illustrated. Such an imaging system 600 is generally designed for use in connection with interventional procedures. The imaging system 600 is characterized by a gantry having a C-arm 602 that carries an x-ray source assembly 604 on one of its ends and an x-ray detector array assembly 606 at its other end. The gantry enables the x-ray source assembly 604 and detector array assembly 606 to be oriented in different locations and angles around a patient disposed on a table 608, while enabling a physician access to the patient.

The gantry includes a support base 610, which may include an L-shaped pedestal that has a horizontal leg 612 that extends beneath the table 608 and a vertical leg 614 that extends upward at the end of the horizontal leg 612 that is spaced from of the table 608. A support arm 616 is rotatably fastened to the upper end of vertical leg 614 for rotation about a horizontal pivot axis 618. The pivot axis 618 is aligned with the centerline of the table 608 and the support arm 616 extends radially outward from the pivot axis 618 to support a C-arm drive assembly 620 on its outer end. The C-arm 602 is slidably fastened to the drive assembly 620 and is coupled to a drive motor (not shown) that slides the C-arm 602 to revolve it about a C-axis 622, as indicated by arrows 624. The pivot axis 618 and C-axis 622 intersect each other at an isocenter 626 that is located above the table 608 and they are perpendicular to each other.

The x-ray source assembly 604 is mounted to one end of the C-arm 602 and the detector array assembly 606 is mounted to its other end. As will be discussed in more detail below, the x-ray source assembly 604 includes an x-ray source (not shown) that emits a cone beam of x-rays, which are directed at the detector array assembly 606. Both assemblies 604 and 606 extend radially inward to the pivot axis 618 such that the center ray of this cone beam passes through the system isocenter 626. The center ray of the cone beam can, thus, be rotated about the system isocenter 626 around either the pivot axis 618, the C-axis 622, or both during the acquisition of x-ray attenuation data from a subject placed on the table 608.

As mentioned above, the x-ray source assembly 604 contains an x-ray source that emits a cone beam of x-rays when energized. The center ray passes through the system isocenter 626 and impinges on a two-dimensional flat panel digital detector housed in the detector assembly 606. Examples of flat panel detectors include so-called "small flat panel" detectors, in which the detector array panel is around 20×20 centimeters in size. Such a detector panel allows the coverage of a field-of-view of around twelve centimeters. Each detector element produces an electrical signal that represents the intensity of an impinging x-ray and, hence, the attenuation of the x-ray as it passes through the patient. During a scan, the x-ray source and detector array are rotated about the system isocenter 626 to acquire x-ray attenuation projection data from different angles. By way of example, the detector array is able to acquire thirty projections, or views, per second. Generally, the numbers of projections acquired per second is the limiting factor that determines how many views can be acquired for a prescribed scan path and speed.

Referring particularly to FIG. 6B, the rotation of the assemblies 604 and 606 and the operation of the x-ray source are governed by a control mechanism 628 of the imaging system 600. The control mechanism 628 includes an x-ray controller 630 that provides power and timing signals to the x-ray source. A data acquisition system ("DAS") 632 in the control mechanism 628 samples data from detector elements in the detector array and passes the data to an image reconstructor 634. The image reconstructor 634, receives digitized x-ray data from the DAS 632 and performs image reconstruction. The image reconstructed by the image reconstructor 634 is applied as an input to a computer 636, which stores the image in a mass storage device 638 or processes the image further.

The control mechanism 628 also includes pivot motor controller 640 and a C-axis motor controller 642. In response to motion commands from the computer 636, the motor controllers 640 and 642 provide power to motors in the imaging system 600 that produce the rotations about the pivot axis 618 and C-axis 622, respectively. A program executed by the computer 636 generates motion commands to the motor controllers 640 and 642 to move the assemblies 604 and 606 in a prescribed scan path.

The computer 636 also receives commands and scanning parameters from an operator via a console 644 that has a keyboard and other manually operable controls. An associated display 646 allows the operator to observe the reconstructed image and other data from the computer 636. The operator supplied commands are used by the computer 636 under the direction of stored programs to provide control signals and information to the DAS 632, the x-ray controller 630, and the motor controllers 640 and 642. In addition, the computer 636 operates a table motor controller 648, which controls the patient table 608 to position the patient with respect to the system isocenter 626.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for determining a three-dimensional location of an interventional medical device using a two-dimensional x-ray image obtained with an x-ray imaging system, the steps of the method comprising:
   a) obtaining x-ray images with the x-ray imaging system;
   b) producing an initial image by down-sampling one of the obtained x-ray images by a down-sampling factor;
   c) determining an initial position estimate of the medical device using the initial image produced in step b);
   d) updating the initial position estimate by iteratively calculating a shift-invariant similarity measure between the initial image and a template image, the template image depicting a synthesized x-ray projection of the medical device positioned at the initial position estimate, in which the initial position estimate and template image are updated in successive iterations and the shift-invariant similarity measure is iteratively calculated until the shift-invariant similarity measure exceeds a threshold value;
   e) refining the updated position estimate by iteratively calculating a shift-variant similarity measure between the image and a template image, the template image depicting a synthesized x-ray projection of the medical device positioned at the updated position estimate, in which the updated position estimate and template image are updated in successive iterations and the shift-variant similarity measure is iteratively calculated until the shift-variant similarity measure exceeds a threshold value; and
   f) determining from the refined position estimate, at least one of the three-dimensional location and orientation of the medical device.

2. The method as recited in claim 1 in which the initial position estimate is updated in step d) by adjusting a depth and three orientation position variables, and in which the updated position estimate is updated in step e) by adjusting a depth and three orientation position variables.

3. The method as recited in claim 1 in which the shift-invariant similarity measure is a normalized cross-correlation, and in which the shift-variant similarity measure is a normalized similarity integral.

4. A method for determining a three-dimensional location of an object using a two-dimensional image obtained with a medical imaging system, the steps of the method comprising:
   a) obtaining images with the medical imaging system;
   b) selecting one of the images obtained in step a);
   c) producing an initial image by down-sampling the image selected in step) by a down-sampling factor;
   d) selecting an initial position estimate of the three-dimensional location of the object;
   e) calculating an updated position estimate by comparing the initial image with a template image of the object, the template image depicting a synthesized projection image of the object positioned in the medical imaging system at a position estimate that is in a neighborhood about the selected initial position estimate;

f) calculating a refined position estimate by comparing the image selected in step b) with an updated template image, the updated template image depicting a synthesized projection image of the object positioned in the medical imaging system at the updated position estimate; and h) determining from the refined position estimate calculated in step f), at least one of the three-dimensional location and orientation of the object.

5. The method as recited in claim 4 in which the downsampling factor is four.

6. The method as recited in claim 4 in which the initial position estimate is selected in step d) by:
   i) calculating a similarity measure between the initial image and a plurality of stored template images, each stored template image depicting a synthesized projection image of the object positioned in the medical imaging system at a different initial position estimate;
   ii) identifying a stored template image that produces the largest similarity measure; and
   ii) selecting the initial position estimate as the different initial position estimate corresponding to the identified stored template image.

7. The method as recited in claim 6 in which the similarity measure calculated in step c)i) is a normalized cross-correlation.

8. The method as recited in claim 4 in which comparing the initial image and the template image in step e) includes calculating a similarity measure therebetween.

9. The method as recited in claim 8 in which the similarity measure is a normalized cross-correlation.

10. The method as recited in claim 9 in which calculating the normalized cross-correlation includes calculating shift values that shift the template image in a plane of the template image using a fast Fourier transform.

11. The method as recited in claim 10 in which calculating the normalized cross-correlation includes calculating a variance of the initial image using sum tables.

12. The method as recited in claim 8 in which step e) is performed iteratively until the similarity measure exceeds a threshold value, in which successive iterations include updating the position estimate and comparing the initial image with a template image depicting a synthesized projection image of the object positioned in the medical imaging system at the updated position estimate.

13. The method as recited in claim 4 in which comparing the image selected in step b) and the template image in step f) includes calculating a similarity measure therebetween.

14. The method as recited in claim 13 in which the similarity measure is a normalized similarity integral.

15. The method as recited in claim 14 in which step f) is performed iteratively until the similarity measure exceeds a threshold value, in which successive iterations include refining the position estimate and comparing the image selected in step b) with a template image depicting a synthesized projection image of the object positioned in the medical imaging system at the refined position estimate.

16. The method as recited in claim 4 in which the medical imaging system is at least one of an x-ray imaging system and a magnetic resonance imaging system.

17. The method as recited in claim 16 in which the x-ray imaging system is a C-arm x-ray imaging system.

18. The method as recited in claim 4 in which the medical imaging system is an x-ray imaging system; and the template images are synthesized x-ray projection images.

19. The method as recited in claim 4 in which the object is at least one of an interventional medical device and a marker.

20. The method as recited in claim 19 in which the interventional medical device is at least one of an electrophysiology catheter and an ablation catheter.

\* \* \* \* \*